United States Patent
Hoang et al.

(10) Patent No.: US 11,463,792 B2
(45) Date of Patent: Oct. 4, 2022

(54) MULTI-CONFIGURABLE HEADSET SUPPORT APPARATUS

(71) Applicant: Safariland, LLC, Jacksonville, FL (US)

(72) Inventors: Peter Hoang, Corona, CA (US); David Le, Irvine, CA (US); Dylan Vaccaro, Jacksonville, FL (US); John Medine, Chino, CA (US)

(73) Assignee: Safariland, LLC, Jacksonville, FL (US)

( * ) Notice: Subject to any disclaimer, the term of this patent is extended or adjusted under 35 U.S.C. 154(b) by 0 days.

(21) Appl. No.: 17/345,749

(22) Filed: Jun. 11, 2021

(65) Prior Publication Data

US 2021/0392424 A1 Dec. 16, 2021

Related U.S. Application Data

(60) Provisional application No. 63/038,344, filed on Jun. 12, 2020.

(51) Int. Cl.
*H04R 1/10* (2006.01)
*A42B 3/30* (2006.01)

(52) U.S. Cl.
CPC ............. *H04R 1/1008* (2013.01); *A42B 3/30* (2013.01); *H04R 1/1033* (2013.01); *H04R 1/1083* (2013.01)

(58) Field of Classification Search
CPC ... H04R 1/00; H04R 1/02; H04R 1/10; H04R 1/1008; H04R 1/1033; H04R 1/105; H04R 1/1058; H04R 1/1066; H04R 1/1083; A42B 3/30; A61F 11/14
See application file for complete search history.

(56) References Cited

U.S. PATENT DOCUMENTS

| 9,973,854 | B1 | 5/2018 | Zimmer |
| 10,102,843 | B1 | 10/2018 | Le et al. |
| D835,076 | S | 12/2018 | Le et al. |
| 10,522,131 | B2 | 12/2019 | Le et al. |

(Continued)

OTHER PUBLICATIONS https://www.ebay.com/itm/184440742004?chn=ps&var=692142658928&norover=1&mkevt=1&mkrid=711-117182-37290-0&mkcid=2&itemid=692142658928_184440742004&targetid=1263433204454&device=c&mktype=pla&googleloc=9031235&poi=&campaignid=11755693593&mkgroupid=122299019677&rlsatarget=pla-1263433204454&abcld=9300462&merchantid=101687876&gclid=EAIaIQobChMIt53UqLH88AIVIYzlChOk7Ad6EAQYBCABEgKEC_D_BwE.
PCT Application No. PCT/US2021/037073—International Search Report and Written Opinion dated Sep. 24, 2021.

*Primary Examiner* — Thang V Tran
(74) *Attorney, Agent, or Firm* — Kane Kessler, P.C.; Barry E. Negrin

(57) ABSTRACT

A multi-configurable headset support apparatus is provided, having at least one earcup having front-facing and rear-facing posts. First and second suspension wires and a helmet mount are each provided with loops at opposite ends that are attachable to the earcup posts. A support band is securable to the suspension wires. When the first suspension wire is attached to the posts and the support band is secured to the first suspension wire, the support band is attached in an upward configuration atop a wearer's head. When the second suspension wire is attached to the posts and the support band is secured to the second suspension wire, the support band is attached in a rearward configuration on the back of the wearer's head. The posts are preferably retractably spring-biased into the earcup; the spring force secures the loop disposed on the post shaft against the earcup via the post head.

25 Claims, 16 Drawing Sheets

(56) References Cited

U.S. PATENT DOCUMENTS

| | | |
|---|---|---|
| 11,011,149 B2 | 5/2021 | Le et al. |
| 2008/0175406 A1* | 7/2008 | Smith .................. H04R 1/1066 381/87 |
| 2014/0259287 A1* | 9/2014 | Waters ............... A41D 13/0002 2/209 |
| 2014/0301590 A1 | 10/2014 | Yang |
| 2017/0214998 A1* | 7/2017 | Hoernschemeyer ......................... H04R 1/1066 |
| 2017/0264984 A1 | 9/2017 | Pelland |
| 2018/0115817 A1* | 4/2018 | Prohaszka .............. H04R 1/105 |
| 2018/0139539 A1* | 5/2018 | Zimmer ............... H04R 1/1008 |
| 2019/0132664 A1 | 5/2019 | Davi et al. |
| 2021/0186140 A1* | 6/2021 | Barber .................... A42B 1/24 |

\* cited by examiner

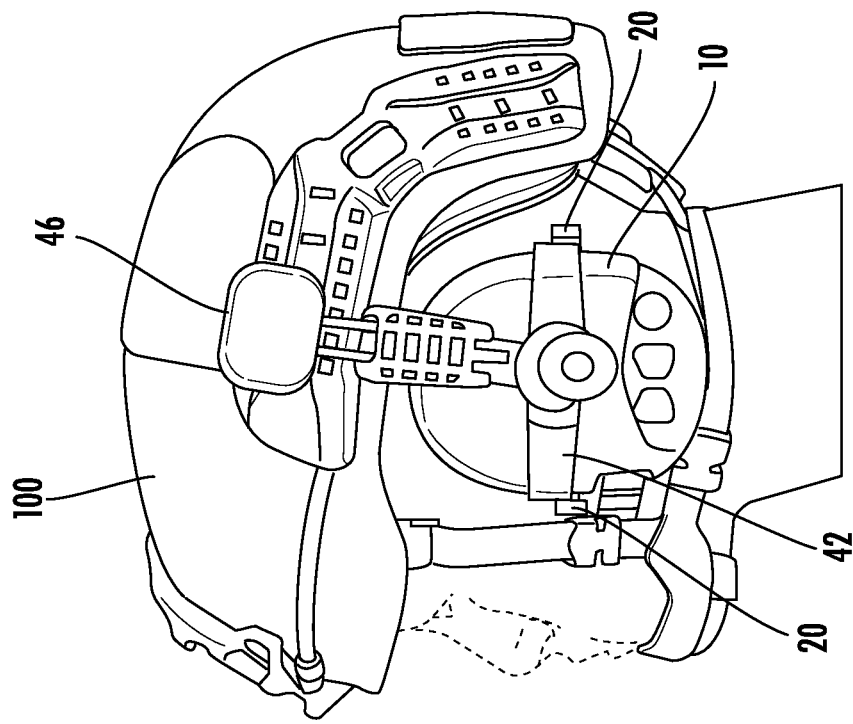
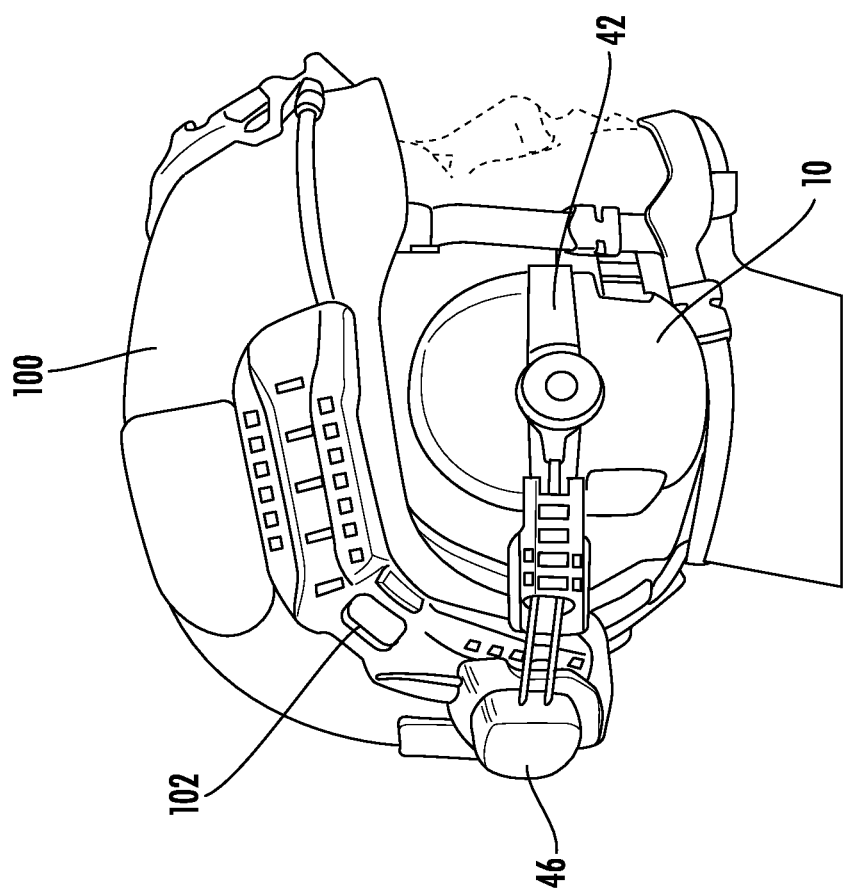

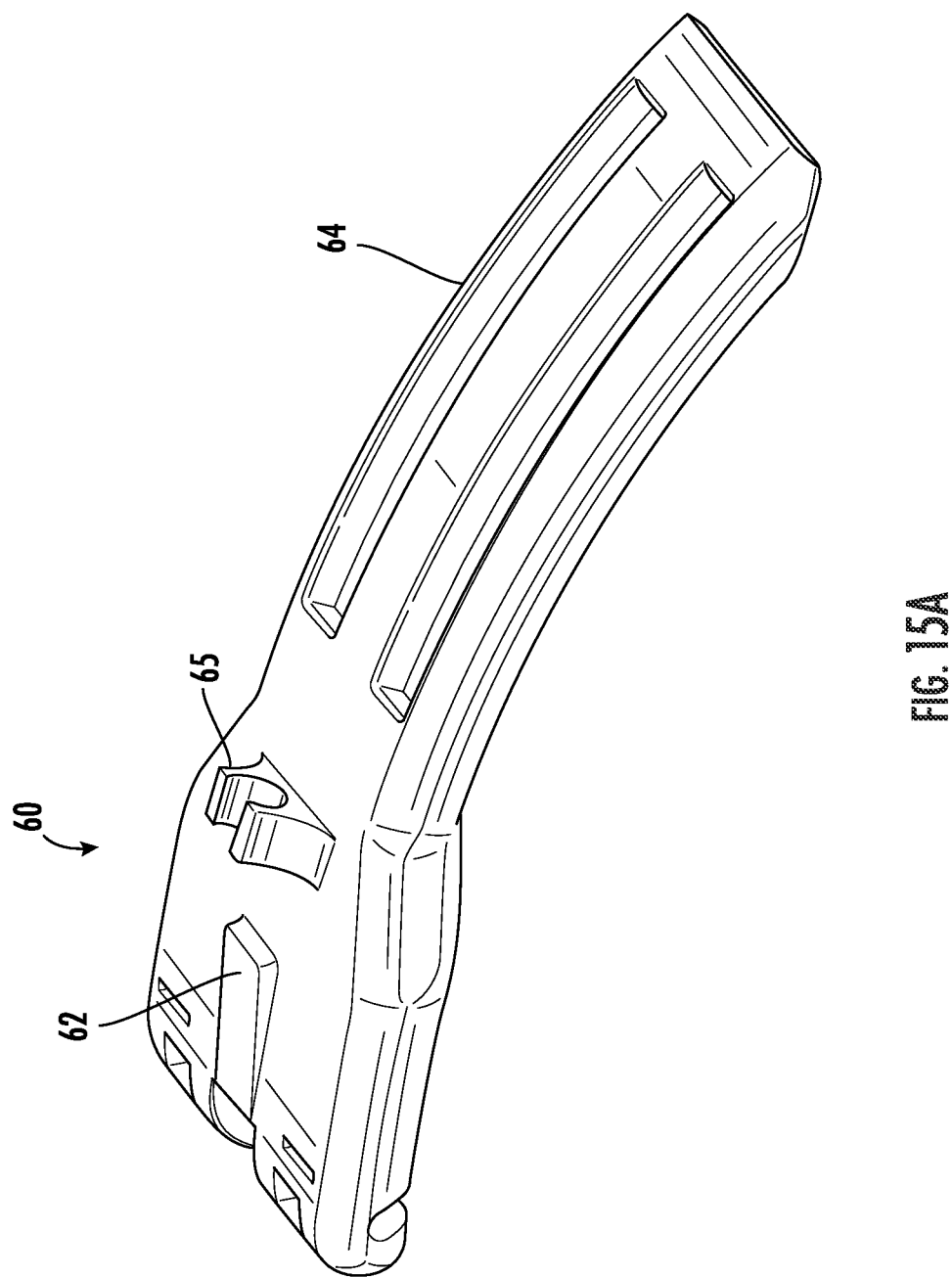

MULTI-CONFIGURABLE HEADSET SUPPORT APPARATUS

RELATED APPLICATIONS

Priority is claimed from U.S. Provisional Patent Application No. 63/038,344 filed Jun. 12, 2020 entitled HEADSET SUPPORT SYSTEM, the entirety of which is incorporated by reference herein.

BACKGROUND OF THE INVENTION

Field of the Invention

The invention is directed to headsets and headset support systems. More specifically, the invention is directed to apparatuses that enable a headset to be changed in physical configuration to the user's preference or needs.

Description of Related Art

Noise cancelling and/or noise reduction headsets are often used by law enforcement, the military, and the like in situations in which ambient noise is very loud and the user needs to hear instructions or communicate with team members over the din. Examples of such a headset are described in U.S. Pat. Nos. 11,011,149; 10,522,131; 10,102,843; and D835,076, the teachings of all of which are incorporated by reference herein.

Such headsets have earcups which are placed over the ears of the user to at least partially block external noise. In many cases, the earcups include one or more speakers which serve several functions. First, instructions or similar communication from a team member or supervisor can be communicated to the wearer. Second, noise cancelling sounds (e.g., sounds having the inverse wave form of external sounds) can be provided over the speakers to cancel out external sounds to nearly completely eliminate them for the wearer.

Such headsets are generally constructed as either being supported by a band on top of the wearer's head, by a band behind the wearer's head, or attached to the wearer's helmet. Unfortunately, these configurations are generally fixed. That is, one would have to purchase separate behind-the-head, over-the-head, and on-the-helmet headsets for different situations. For example, some uniforms, bomb suits, and tactical gear have a neck protector that might interfere with a behind-the-head headset support structure. As another example, there may be situations when the user will be wearing a helmet or similar head protection that would interfere with an over-the-head support band. Conversely, there may be situations where the user will not be wearing a helmet, thereby rendering ineffective an on-the-helmet headset. Often, the user simply has a preference for one of these configurations and may be locked into a less-preferred configuration.

Accordingly, there is a long-felt need to provide a headset support system/apparatus that is flexible in use and can be configured in more than one way. There is another long-felt need to provide a headset support system/apparatus that can be reconfigured easily among behind-the-head, over-the-head, and on-the-helmet configurations.

SUMMARY OF THE INVENTION

The invention relates to a headset support system. The system enables a user to wear a headset in any one of three configurations—supporting the earcups with a band over the head, supporting the earcups with a band behind the head, or supporting the earcups via helmet rail connectors.

The support system includes structure that connects the earcups with the selected band or rail connector (for convenience, that will be referred to hereinafter as a band). Each earcup includes two connectors or posts, front and back, for connection with the band. The two connectors are preferably identical to each other. The connectors are configured to receive wire loops as shown on the ends of a suspension wire connector on the band, or alternatively a loop on the end of a bracket on a rail connector. The connector releasably captures the wire loop on the earcup.

The connector preferably includes an internally threaded insert that is fixed in the earcup. The connector also preferably includes a spring plunger assembly (which includes a plunger and an externally threaded sleeve) that is screwed into the insert. The sleeve ends up in a fixed position in the earcup. The plunger is slidable into and out of the sleeve. The plunger is spring biased inward, relative to the sleeve, by a tension spring.

There are two keys or key slots on the underside of the plunger head. The keys or key slots can fit into/onto two corresponding prongs/slots keyways on the outer end of the sleeve, when the parts are in a particular rotational orientation.

To open the connector post, the user pulls the plunger straight out against the bias of the spring, pulling the keys out of the keyways (or vice versa). That longitudinal movement enables the plunger to be rotated relative to the sleeve. If the plunger is turned 90 degrees, it will stay open by itself (temporarily). Then the user places the loop over the connector. This loop could be the wire loop of the on-the-head band or the behind-the-neck band, or it could be the bracket of the rail connector. When the plunger is pulled open, that movement exposes a narrow diameter portion of the shank. The loop is slipped over that narrow diameter portion.

Then the plunger is rotated until the keys align with the keyways. Releasing the outward force on the plunger will enable the plunger to be pulled down by the spring down into engagement with the loop. A larger diameter portion of the plunger shank is inside the loop, providing a secure fit. A still larger diameter head prevents the loop from slipping off the connector post.

The invention includes a multi-configurable headset support system. At least one earcup has a front-facing post and a rear-facing post. A first suspension wire has a first loop at a first end and a second loop at a second end, the first and second loops configured to be releasably attachable to the front-facing post and the rear-facing post, respectively. A second suspension wire has a third loop at a third end and a fourth loop at a fourth end, the third and fourth loops configured to be releasably attachable to the front-facing post and the rear-facing post, respectively. A support band is selectively individually securable to the first and second suspension wires at a time (i.e., one or the other at a time). When the first suspension wire is attached to the front-facing post and the rear-facing post and the support band is secured to the first suspension wire, the support band is attached in an upward configuration to be disposed on the top of a wearer's head. When the second suspension wire is attached to the front-facing post and the rear-facing post and the support band is secured to the second suspension wire, the support band is attached in a rearward configuration to be disposed on the back of the wearer's head. The first suspension wire is preferably substantially U-shaped. The second suspension wire includes a U-shaped section and a rearwardly projecting section, with the third loop being formed on the U-shaped section and the fourth loop being formed on the rearwardly projecting section, the support being securable to the rearwardly projecting section.

Preferably, the inventive headset support system also includes a helmet mount having a bracket, the bracket having a fifth loop at a fifth end and a sixth loop at a sixth end, the fifth and sixth loops configured to be releasably attachable to the front-facing post and the rear-facing post, respectively. The helmet mount also includes a helmet rail mount configured to be attachable to a rail of a helmet.

Although the headset apparatus of the invention can include one of all of the above components, it preferably includes two of the earcups, two of the first suspension wires, two of the second suspension wires, and two of the helmet mounts.

In one embodiment, the front-facing post and the rear-facing post each has a longitudinal shaft and a head wider than the shaft, wherein the loops of the first and second suspension wires attach around the shafts of the front-facing post and the rear-facing post and are at least partially secured by the heads of the front-facing post and the rear-facing post. At least one of (and preferably both of) the front-facing post and the rear-facing post is retractably spring-biased into the earcup by a spring. Force generated by the spring of the at least one of the front-facing post and the rear-facing post secures the loop disposed on the shaft against the earcup via the head.

In one embodiment, the shaft includes an outer tube fixedly secured to the earcup and an inner plunger reciprocatably disposed inside the outer tube, the head attached to a distal end of the inner plunger. A spring connects the outer tube and the inner plunger biasing the inner plunger into the outer tube. In one embodiment, the outer tube includes distal prongs and the head comprising key slots formed on a proximal surface of the head and configured to receive the distal prongs. The inner plunger is rotatable with respect to the outer tube when the inner plunger is at least partially withdrawn from the outer tube and the distal prongs are not in engagement with the key slots. When the inner plunger is at least partially withdrawn from the outer tube, the inner plunger is rotatable to a fixed extended position in which the distal prongs of the outer tube contact the proximal surface of the head and are not disposed in the key slots.

In one embodiment, the shaft includes prongs formed on one of the outer tube and the head, and key slots formed on the other of the outer tube and the head and configured to receive the prongs. The inner plunger is rotatable with respect to the outer tube when the inner plunger is at least partially withdrawn from the outer tube and the prongs are not in engagement with the key slots. When the inner plunger is at least partially withdrawn from the outer tube, the inner plunger is rotatable to a fixed extended position in which the prongs are not disposed in the key slots.

In one embodiment, the head of the post includes a proximal hub wider than the shaft, and the loops of the first and second suspension wires each includes an opening wider than the shaft and narrower than the hub. The hub fits within the loop secured on the shaft to help secure the loop on the earcup.

In one embodiment, the head of the post includes a proximal hub wider than the shaft, and the loops of the first and second suspension wires each includes an opening wider than the shaft and narrower than hub. The hub fits within and is spring-biased within the loop secured on the shaft to help secure the loop on the earcup.

In one embodiment, the earcup further includes a speaker to provide sound to the wearer and insulation configured to at least partially block external sounds from the wearer.

The invention also includes a multi-configurable headset support system enabling configuring of headset earcups in multiple ways on a user's head. At least one retractable post is mounted on an earcup; the post has a longitudinal shaft and a head wider than the shaft. A suspension wire has a loop at an end of the wire, the loop being configured to be releasably attachable to the retractable post when the post is in an extended position. A support band is securable to the suspension wire. When the loop is attached to the shaft and the post is retracted to a retracted position, the head secures the loop against the earcup. The shaft preferably includes an outer tube fixedly secured to the earcup and an inner plunger reciprocatably disposed inside the outer tube, the head being attached to a distal end of the inner plunger. A spring connects the outer tube and the inner plunger, biasing the inner plunger into the outer tube. The shaft further includes prongs formed on one of the outer tube and the head and key slots formed on the other of the outer tube and the head and configured to receive the prongs. The inner plunger is rotatable with respect to the outer tube when the inner plunger is at least partially withdrawn from the outer tube and the prongs are not in engagement with the key slots.

In one embodiment, the head includes a proximal hub wider than the shaft, and the loop of the suspension wire has an opening wider than the shaft and narrower than hub. The hub fits within and is spring-biased within the loop secured on the shaft to help secure the loop on the earcup.

BRIEF DESCRIPTION OF THE DRAWINGS

FIG. 13A is a side elevation view of the apparatus of FIG. 12 in use as a rear rail mount in accordance with an embodiment of the invention.

FIG. 13B is a side elevation view of the apparatus of FIG. 12 in use as a top rail mount in accordance with an embodiment of the invention.

FIG. 15A is a top perspective of a headband size adjustment slide in accordance with an embodiment of the invention.

DETAILED DESCRIPTION OF THE INVENTION AND DRAWINGS

Description will now be given with reference to the attached FIGS. 1-15. It should be understood that these figures are exemplary in nature and in no way serve to limit the scope of the invention, which is defined by the claims appearing hereinbelow.

Figure 1:
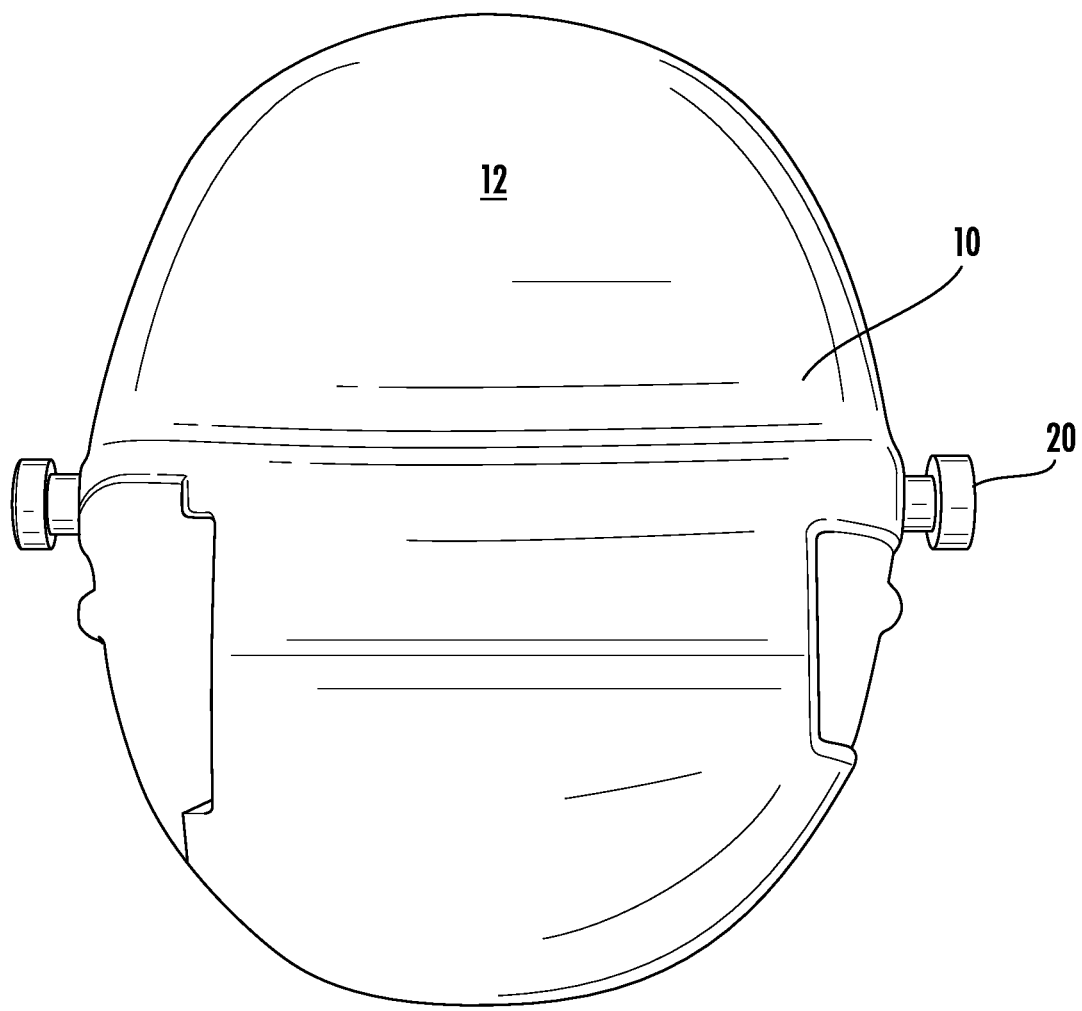
FIG. 1 is a front elevation view of an earcup of a headset support apparatus in accordance with an embodiment of the invention.

As shown in FIG. 1, earcup 10 is generally of the typical type used in a noise protection headset. That is, it includes an outer shell 12 and, typically, some form of insulation (not shown) that reduces the amount of sound that reaches the wearer's ears. Earcup 10 also typically includes at least one speaker (not shown) that provides sound to the wearer: either noise cancelling sound to further reduce/eliminate the ambient sounds that reach the ear of the wearer and/or active sounds such as those from a communication channel shared with peers.

Earcup 10 also includes at least one and preferably two connector posts 20. They are preferably disposed on a front-facing surface and a rear-facing surface, respectively, of earcup 10 ("front-facing" and "rear-facing" meaning the directions when the earcup is being worn, i.e., pointing towards the front and rear of the wearer, respectively). A variety of headset suspension structures to be described below are releasably attachable to connector posts 20.

Figure 2:
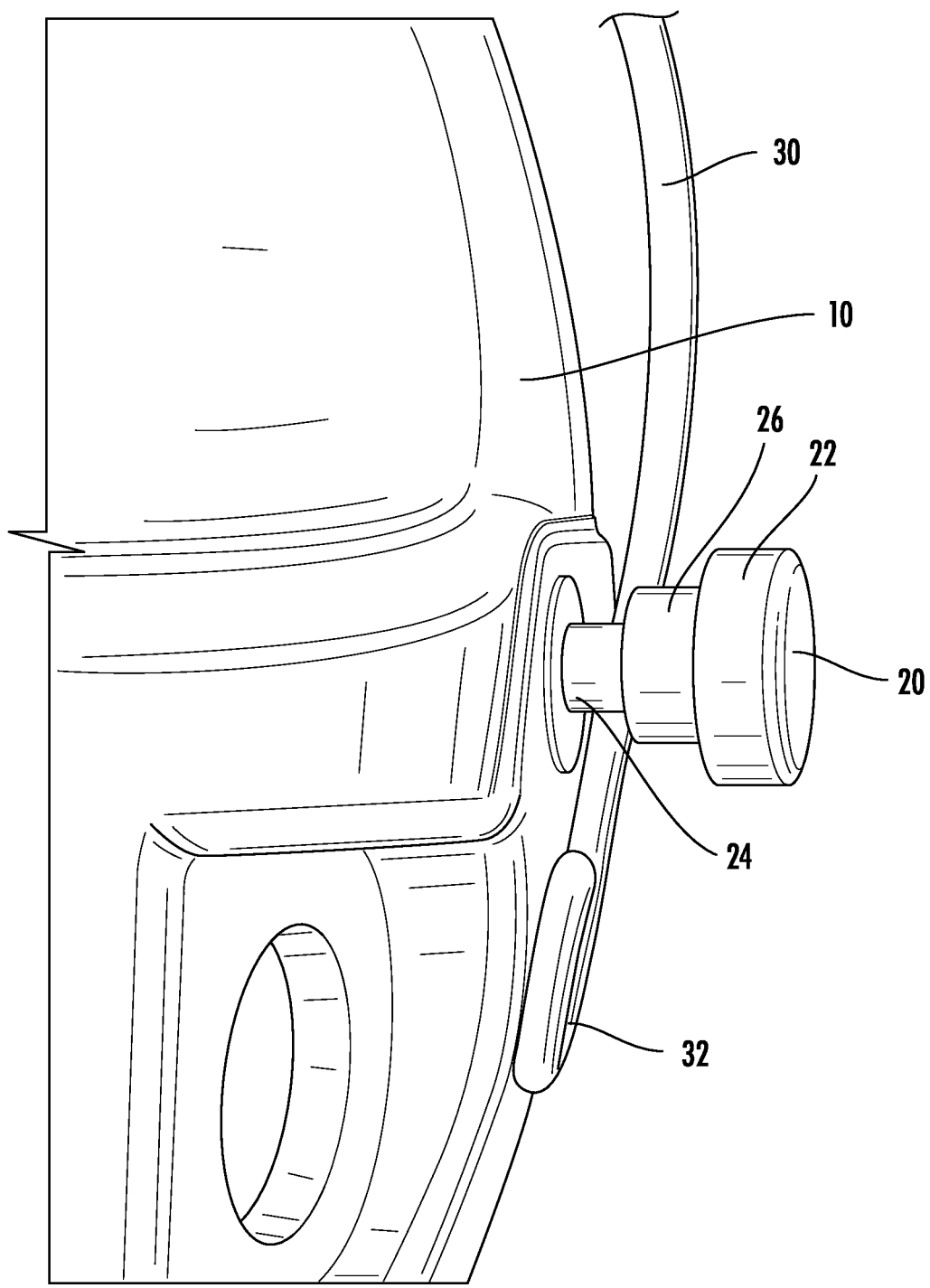
FIG. 2 is a perspective view of a securing post and a support wire loop of a headset support apparatus in accordance with an embodiment of the invention.
Figure 3:
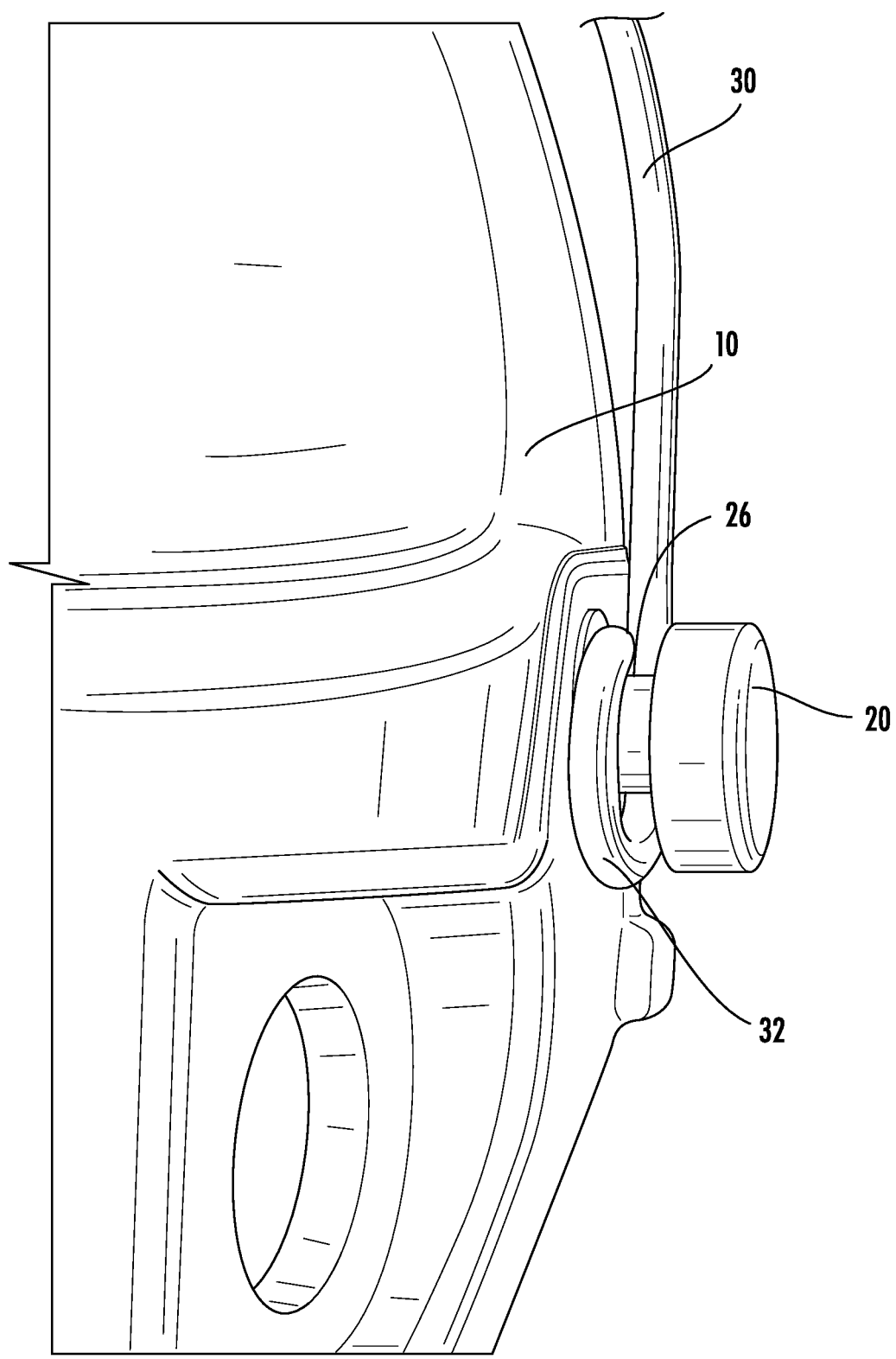
FIG. 3 is a perspective view of the securing post and the support wire loop of FIG. 2 with the latter secured to the former in accordance with an embodiment of the invention.

FIGS. 2 and 3 show additional details of connector post 20 and the interaction it has with the headset suspension structures. Connector post 20 preferably includes head 22 fixed on shaft 24. Head 22 is preferably knurled or otherwise provided with a no-slip surface or has a high coefficient of friction to facilitate its manipulation. The proximal side of head 22 includes a hub 26 to be described later, and connected to hub 26 is a shaft 24. As shown in FIG. 2, post 20 can be at least partially withdrawn from earcup 10 to expose shaft 24.

FIGS. 2 and 3 also depict the end of a suspension wire 30 which is to be secured to earcup 10 and to a headset support band in a manner to be described below. Suspension wire 30 has at each of its ends hooks/loops 32. In operation, posts 20 are withdrawn from earcup 10 to expose shafts 24, and loops 32 are placed on shafts 24. Then, as shown in FIG. 3, posts 20 are retracted back into earcup 10. Hub 26 sits within loop 32 to help secure it to the earcup. In one embodiment, loop 32 is not entirely closed but has an opening that is slightly larger than the diameter of shaft 24 but smaller than the diameter of hub 26 (and certainly smaller than the diameter of head 22 in the event that no hub is provided). That way, when post 20 is retracted into earcup 10, hub 26 helps prevent loop 32 from coming off of post 20.

To help ensure that post 20 stays retracted when retracted and stays withdrawn when withdrawn, a locking mechanism is preferably provided, one embodiment of which is best shown in FIGS. 4A-E. Shaft 24 includes an outer tube 23 that is secured to, e.g., screwed or glued into, earcup 10. Disposed within outer tube 23 is a reciprocatable plunger 25 that is secured to head 22/hub 26. Spring 29 is provided connected between plunger 25 and outer tube 23 to maintain the position of plunger 25 within tube 23 under unloaded conditions. The user must pull on head 22 and overcome the spring force of spring 29 to withdraw plunger 25 from tube 23.

Figure 4A:
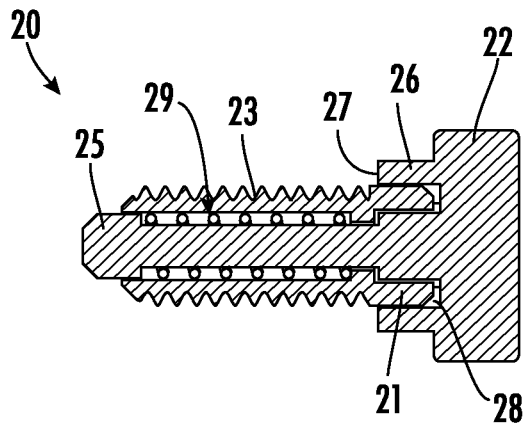
FIG. 4A is a sectional view of a securing post in a retracted configuration in accordance with an embodiment of the invention.
Figure 4B:
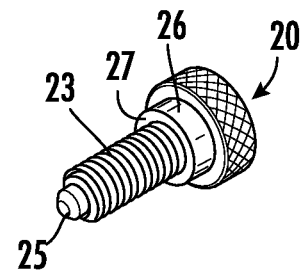
FIG. 4B is a perspective view of the securing post of FIG. 4A.
Figure 4C:
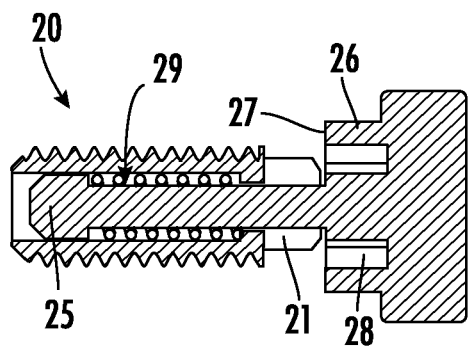
FIG. 4C is a sectional view of the securing post of FIGS. 4A-B in an extended configuration.
Figure 4D:
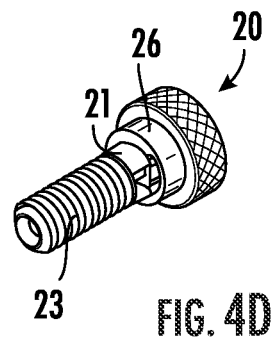
FIG. 4D is a perspective view of the securing post of FIG. 4C.
Figure 4E:
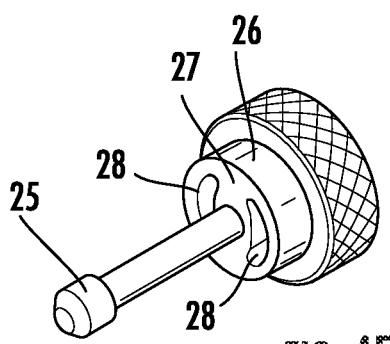
FIG. 4E is a perspective view of an inner plunger of a securing post in accordance with an embodiment of the invention.

Formed on the underside or proximal surface 27 of hub 26 are key slots 28 (see FIG. 4E as well) which receive prongs 21 formed on the distal end of outer tube 23. FIGS. 4A and 4B depict post 20 in its retracted position, i.e., with prongs 21 disposed inside key slots 28. When the user pulls on head 22 of post 20 to withdraw post 20 from earcup 10, prongs 21 are disengaged from key slots 28. If the user wishes to maintain post 20 in its extended position, the user can rotate head 22 to take key slots 28 out of alignment with prongs 21. Then, when the user lets go of head 22, spring 29 will bias plunger 25 downward towards earcup 10, however hub proximal surface 27 will engage outer tube prongs 21 and prevent plunger 25 from moving downward any further, as shown in FIGS. 4C and 4D. The user is then free to attach a suspension structure to the exposed portion of post 20, turn head 22 to realign key slots 28 with prongs 21, and then let go of head 22 to allow key slots 28 to re-engage prongs 21 and thus to allow plunger 25 to move all the way back down into outer tube 23.

Figure 5:
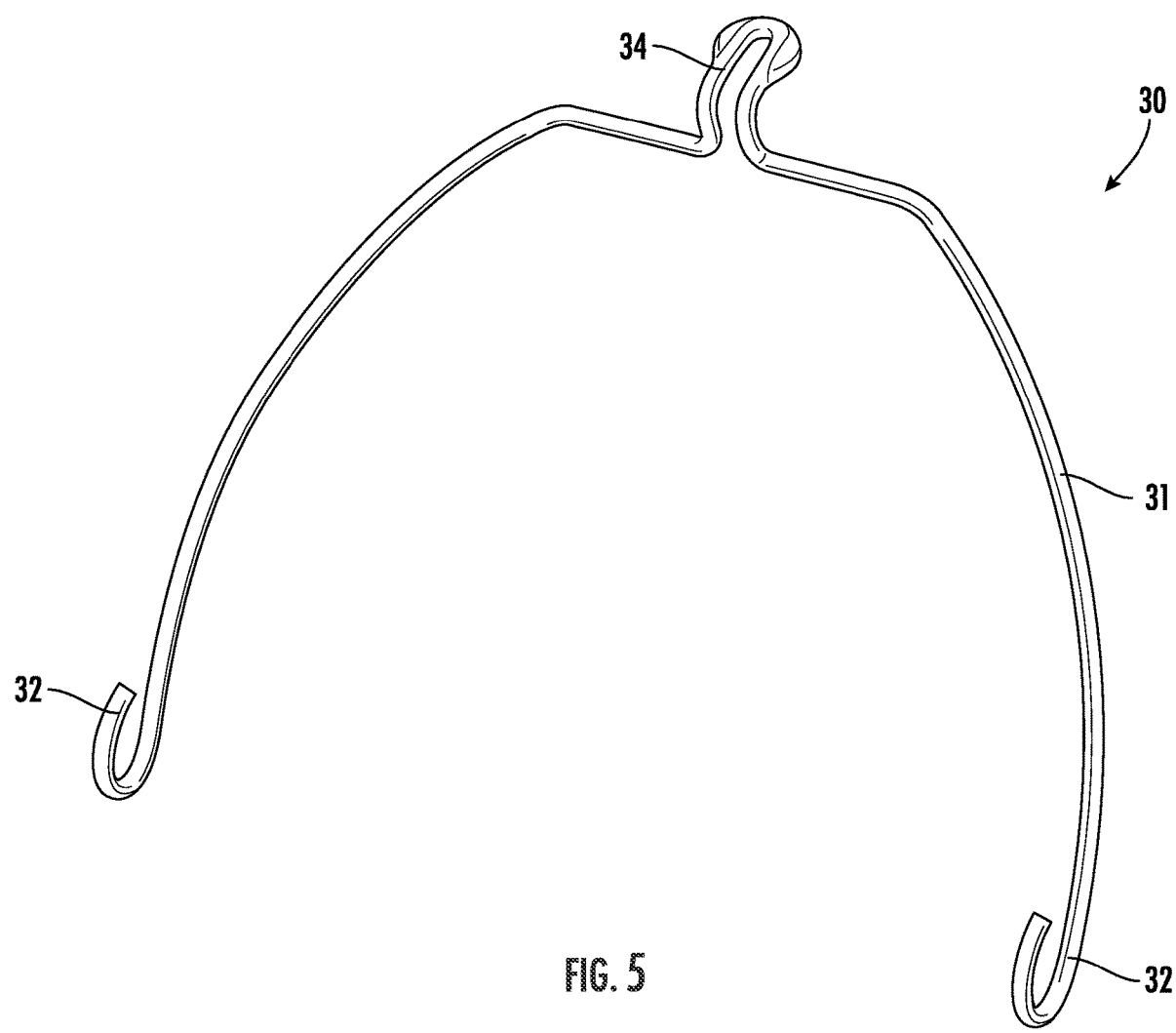
FIG. 5 is a perspective view of an over-the-head suspension wire in accordance with an embodiment of the invention.
Figure 6:
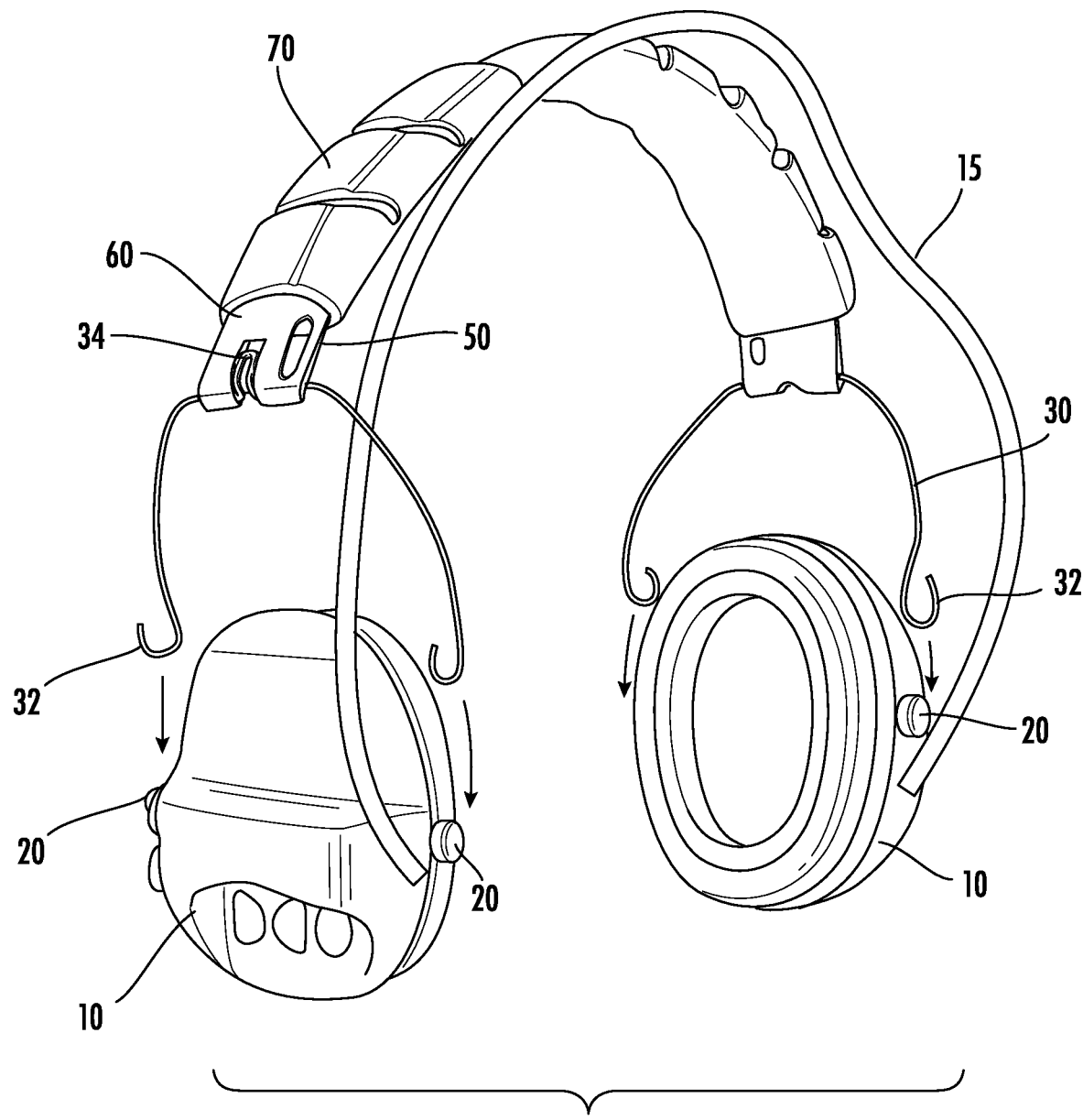
FIG. 6 is a perspective view of two suspension wires of FIG. 5 being attached to two earcups of FIG. 1 in accordance with an embodiment of the invention.
Figure 7:
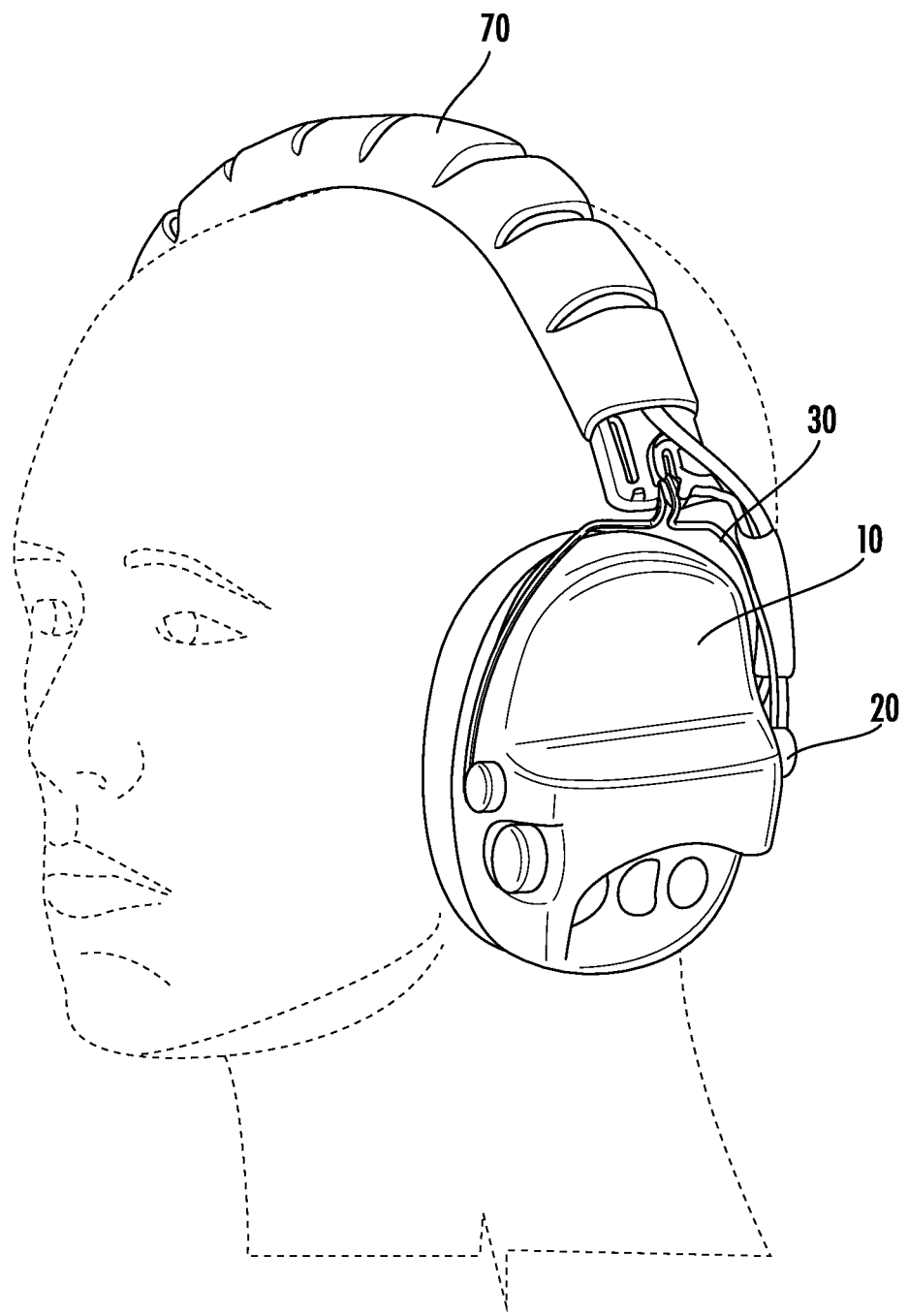
FIG. 7 is a perspective view of the apparatus of FIG. 6 in use in accordance with an embodiment of the invention.

Description will now be given for specific configurations of the apparatus. FIGS. 5-7 depict one embodiment of an upward, i.e., over-the-head, earcup suspension configuration. FIG. 5 depicts suspension wire 30, an over-the-head suspension wire. Wire 30 includes a main substantially U-shaped body 31 having loops 32 at either end. Loops 32 of wire 30 are substantially as described above: that is, they are preferably open loops that can be placed on shafts 24 of posts 20 and locked thereon by hubs 26 when posts 20 are retracted into earcup 10. Headband securing prong 34 is formed in the substantially U-shaped body 21 of suspension wire 30 and is to be connected to a headband, e.g., to be described below.

As shown in FIG. 6, in one embodiment, two earcups 10 are provided, and two suspension wires 30 are provided to secure the earcups to the headband. Because headband securing prongs 34 are formed substantially in the centers of wires 30, the two over-the-head suspension wires in this embodiment are substantially identical and can be used on either the left or right earcup. The user extends posts 20 from earcups 10 and rotates them to keep posts 20 in an extended position by disengaging and unaligning prongs 21 from key slots 28. Loops 32 are secured to posts 20 as shown by the arrows, and then posts 20 are retracted back into earcups 10. Headband securing prongs 34 of suspension wires 30 are secured to headband slide 60. Wire 15 connecting the two earcups 10 is secured to headband 50 via cover 70. The resulting upward, over-the-head configuration is shown in its final form in FIG. 7.

Figure 8:
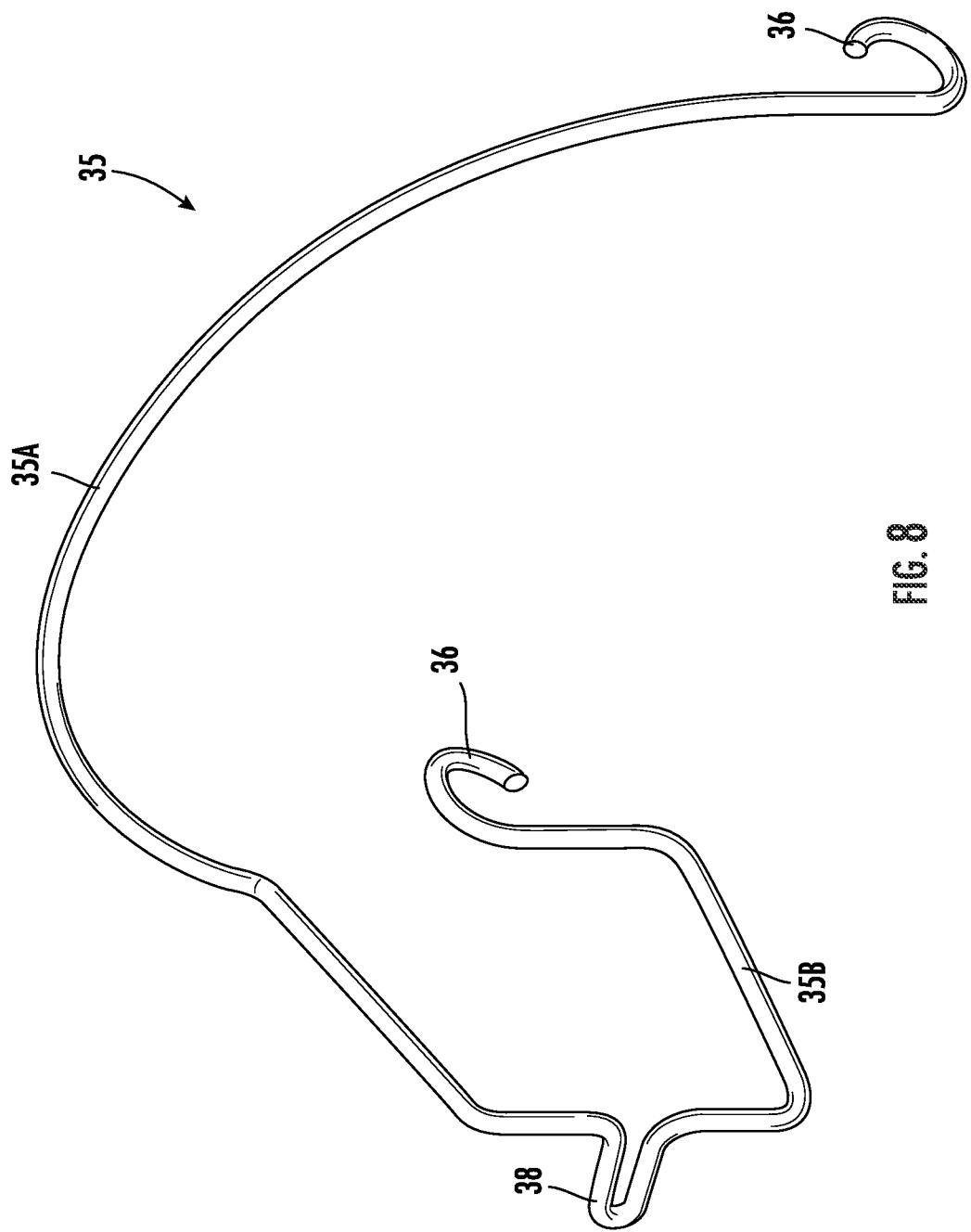
FIG. 8 is a perspective view of a behind-the-head suspension wire in accordance with an embodiment of the invention.
Figure 9:
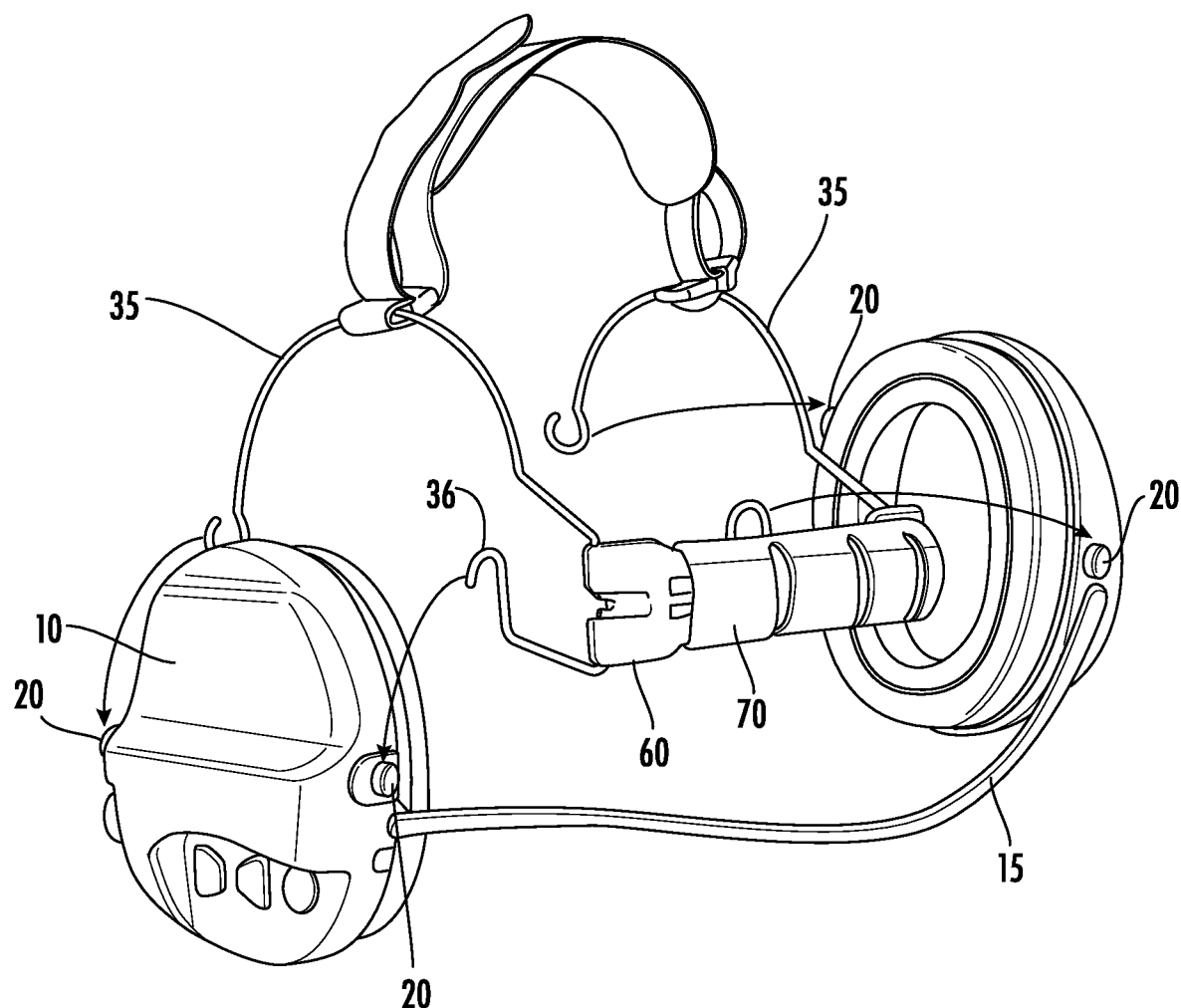
FIG. 9 is a perspective view of two suspension wires of FIG. 8 being attached to two earcups of FIG. 1 in accordance with an embodiment of the invention.
Figure 10:
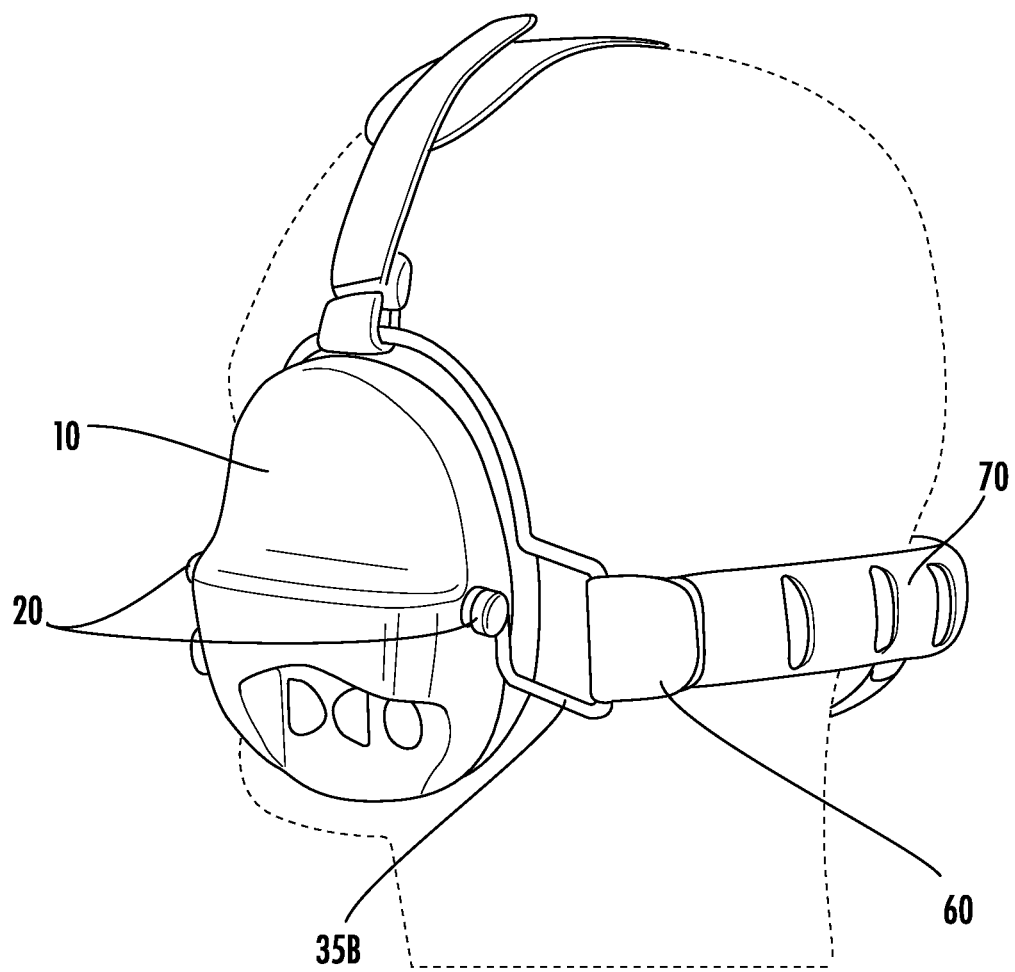
FIG. 10 is a rear perspective view of the apparatus of FIG. 9 in use in accordance with an embodiment of the invention.

FIGS. 8-10 depict one embodiment of a rearward, i.e., behind-the-head, earcup suspension configuration. FIG. 8 depicts suspension wire 35, a behind-the-head suspension wire. Wire 35 includes a U-shaped section 35A having a loop 36 at its end and a rearwardly projecting section 35B having a loop 36 at its end. As above, loops 36 of wire 35 are preferably open loops that can be placed on shafts 24 of posts 20 and locked thereon by hubs 26 when posts 20 are retracted into earcup 10. Headband securing prong 38 is formed in rearwardly projecting section 35B of suspension wire 30 and is to be connected to a headband.

As shown in FIG. 9, in one embodiment, two earcups 10 are provided, and two suspension wires 35 are provided to secure the earcups to the headband. Because headband securing prongs 38 are formed in the rearwardly projecting portions 35B of wires 35, the two behind-the-head suspension wires in this embodiment are mirror images of each other rather than identical. The user extends posts 20 from earcups 10 and rotates them to keep posts 20 in an extended position by disengaging and unaligning prongs 21 from key slots 28. Loops 36 are placed on posts 20 as shown by the arrows, and then posts 20 are retracted back into earcups 10. Headband securing prongs 38 of suspension wires 35 are secured to headband slide 60. Wire 15 connecting the two earcups 10 is secured to headband 50 via cover 70. The resulting rearward, behind-the-head configuration is shown in its final form in FIG. 10. Extra support may be provided by an additional band 80 secured to U-shaped portions 35A of wires 35.

Figure 11:
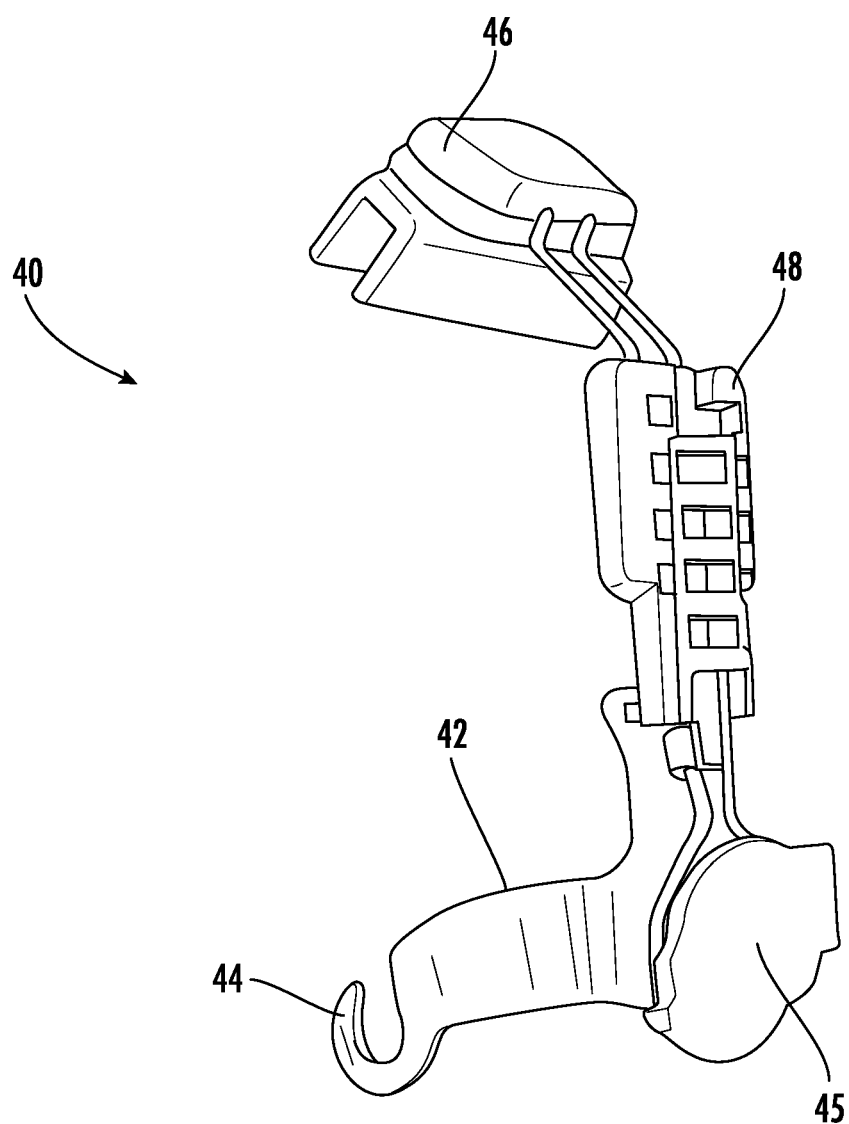
FIG. 11 is a perspective view of a helmet mount in accordance with an embodiment of the invention.
Figure 12:
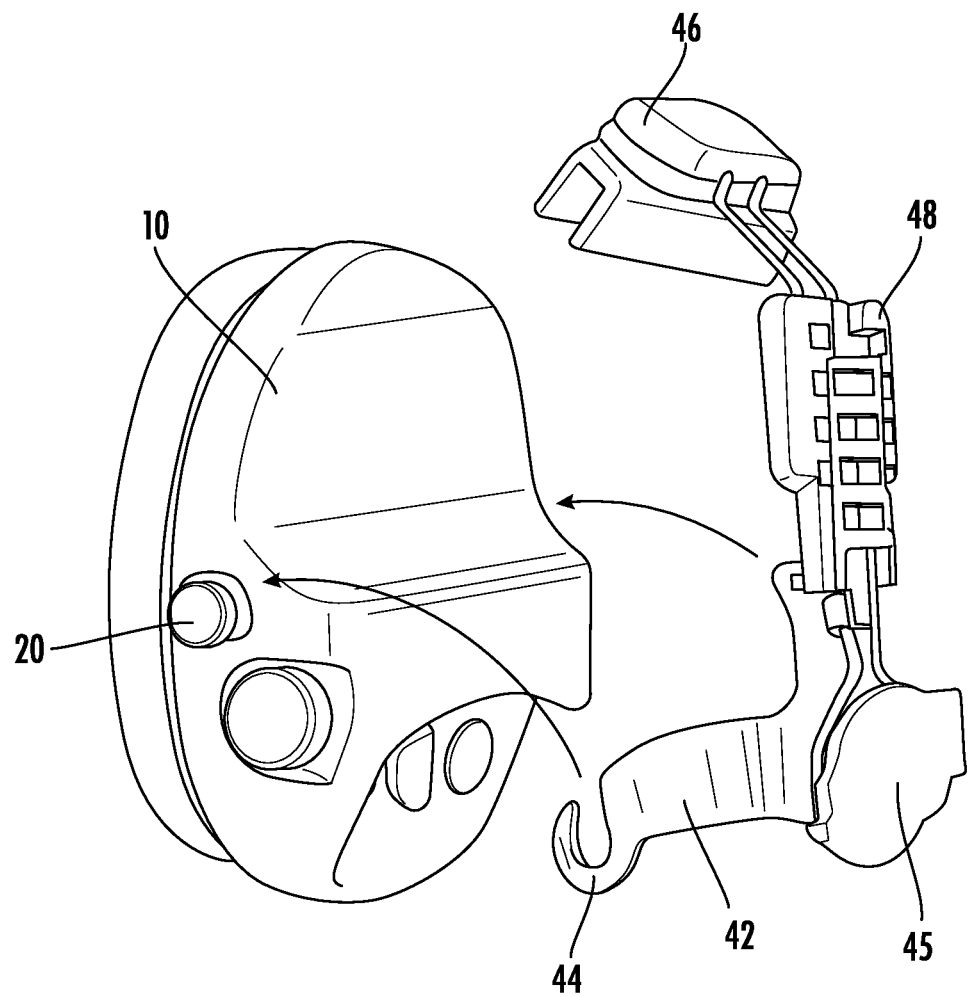
FIG. 12 is a perspective view of one helmet mount of FIG. 11 being attached to an earcup of FIG. 1 in accordance with an embodiment of the invention.

FIGS. 11-13 depict one embodiment of a helmet mount suspension configuration. FIG. 11 depicts helmet mount 40. Helmet mount 40 has at one end an earcup bracket 42, which has open loops 44 at either end thereof. Loops 44 are securable to earcup posts 20 in the same manner as described above. In a central portion of bracket 42 is hub 45 that enables the rest of mount 40 to rotate with respect to bracket 42 to accommodate different helmet rails. At the other end of mount 40 is helmet rail mount 46 for attaching mount 40 to a helmet having a rail mounting system. Helmet rail mounting systems are known and described in, for example, U.S. Pat. Nos. 10,350,113 and 10,582,736, the teachings of both of which are incorporated by reference herein. Mount 40 may also include a slide lock switch 48 for adjusting the length of mount 40 to accommodate different sizes of users' heads.

As shown in FIG. 12, the user extends posts 20 from earcup 10 and rotates them to keep posts 20 in an extended position by disengaging and unaligning prongs 21 from key slots 28. Loops 44 are secured to posts 20 as shown by the arrows, and then posts 20 are retracted back into earcups 10. Helmet rail mount 46 is attached to rail 102 of helmet 100 (FIGS. 13A-B). FIG. 12 depicts a single earcup 10; either one or two earcups may be provided in any embodiment and any securing configuration (although two earcups are typically preferred).

In FIG. 13A, helmet rail mount 46 is attached to helmet rail 102 at a rear portion of helmet 100; mount 40 is rotated around hub 45 to be substantially parallel to earcup bracket 42. In FIG. 13B, helmet rail mount 46 is attached to helmet rail 102 at a top portion of helmet 100; mount 40 is rotated around hub 45 to be substantially perpendicular to earcup bracket 42.

Figure 14:
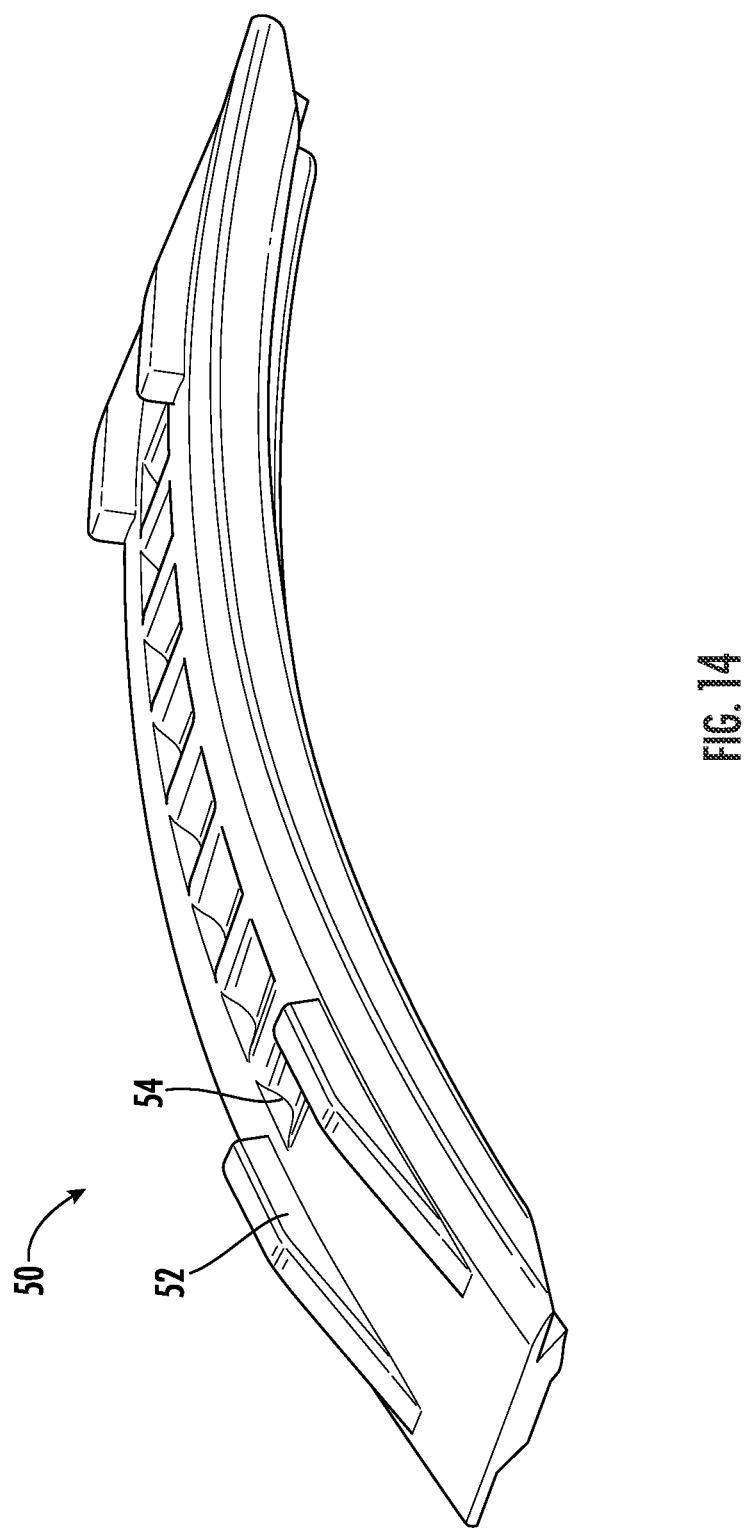
FIG. 14 is a side perspective of a support headband in accordance with an embodiment of the invention.
Figure 15B:
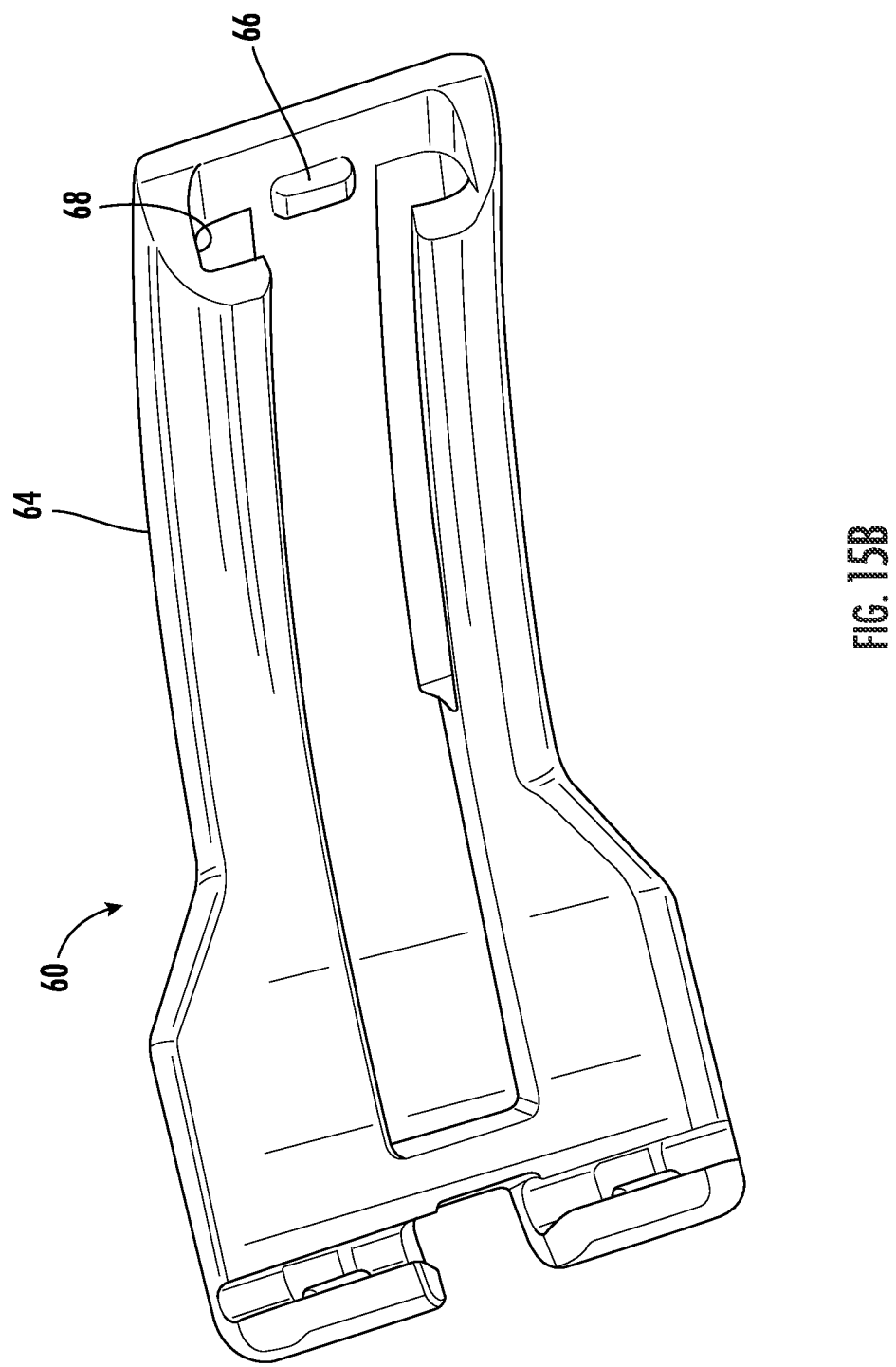
FIG. 15B is a bottom perspective of the headband size adjustment slide of FIG. 15A.

One embodiment of a headband in accordance with the invention is depicted in FIGS. 14-15. Headband 50 includes ramps 52 and central detent divots 54. FIGS. 15A-B depict one embodiment of a headband adjustment slide. Slide 60 includes a ramp 62 configured to engage with headband securing prongs 34 and 38 of suspension wires 30 and 35. Bracket 65 is provided to secure wire 15 firmly to headband 50 via slides 60 to prevent wire 15 from rattling against headband 50 and making undesirable noise, as well as to protect wire 15. As shown in FIG. 15B, main section 64 includes arms 68 which wrap around headband 50 and detent 66 which engages with detent divots 54. Slide 60 can be moved along headband 50 to make the overall length of the headband assembly longer or shorter as desired. Typically, two slides 60 are provided.

It can be seen from the above description that the invention offers great flexibility in allowing the user to reconfigure the same headset gear easily amongst three different configurations (over-the-head, behind-the-head, and on-the-helmet).

The invention is not limited to the above description. For example, the drawings and description depict prongs disposed on the outer tube of the post and corresponding key slots formed in the proximal side of the head. However, those can be reversed; that is, prongs may be formed on the proximal side of the head and corresponding key slots can be formed on the distal end of the outer tube. As another alternative, prongs can be formed on the proximal end of the plunger that are rotatably lockable into slots formed internally within the earcup, either in the shell itself or on an additional structure, having, for example, L-shaped grooves that the prongs can be pulled into and then rotated into to lock them therein, or a detent mechanism. As another alternative, the connector posts need not be spring-biased; instead, they may be provided with click-lock detent structures at the top and bottom of the reciprocatable stroke of the plunger/shaft to enable the shaft to remain securely either in the extended or retracted positions. Similar locking mechanisms can be used in addition or the alternative without departing from the scope of the invention. As another alternative, rather than providing two posts, front-facing and rear-facing, on each earcup, a single more centrally-located retractable post can be provided on each earcup with a corresponding suspension wire having a single loop to be secured thereto. In that embodiment, the suspension wire can rotate about the retractable post and support a head band on top of the wearer's head, behind the wearer's head, or any intermediate position therebetween.

Additionally, the invention it is not limited to military, emergency, and law enforcement uses. For example, concerts, sporting events, and construction sites all often provide exceptionally loud ambient atmospheres (e.g., from music, crowd noise, or construction equipment) over which attendees/workers may want to hear announcements or communicate with each other while protecting their hearing. The flexibility of the invention allows the same device to be used in a variety of situations, such as wearing a hat while attending an outdoor event, wearing a construction helmet on site, etc. where the user needs several options on how to deploy the same headset.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

What is claimed is:

1. A multi-configurable headset support system, comprising:
   at least one earcup having a front-facing post and a rear-facing post;

a first suspension wire having a first loop at a first end and a second loop at a second end, said first and second loops configured to be releasably attachable to said front-facing post and said rear-facing post, respectively;

a second suspension wire having a third loop at a third end and a fourth loop at a fourth end, said third and fourth loops configured to be releasably attachable to said front-facing post and said rear-facing post, respectively; and a support band selectively individually securable to said first and second suspension wires at a time, wherein when said first suspension wire is attached to said front-facing post and said rear-facing post and said support band is secured to said first suspension wire, said support band is attached in an upward configuration to be disposed on the top of a wearer's head, and wherein when said second suspension wire is attached to said front-facing post and said rear-facing post and said support band is secured to said second suspension wire, said support band is attached in a rearward configuration to be disposed on the back of the wearer's head.

2. A multi-configurable headset support system according to claim 1, wherein said first suspension wire is substantially U-shaped, and wherein said second suspension wire includes a U-shaped section and a rearwardly projecting section, with said third loop being formed on said U-shaped section and said fourth loop being formed on said rearwardly projecting section, said support being securable to said rearwardly projecting section.

3. A multi-configurable headset support system according to claim 1, further comprising a helmet mount having:

a bracket, said bracket having a fifth loop at a fifth end and a sixth loop at a sixth end, said fifth and sixth loops configured to be releasably attachable to said front-facing post and said rear-facing post, respectively; and a helmet rail mount configured to be attachable to a rail of a helmet.

4. A multi-configurable headset support system according to claim 1, further comprising two of said earcups, two of said first suspension wires, and two of said second suspension wires.

5. A multi-configurable headset support system according to claim 3, further comprising two of said earcups, two of said first suspension wires, two of said second suspension wires, and two of said helmet mounts.

6. A multi-configurable headset support system according to claim 1, said front-facing post and said rear-facing post each having a longitudinal shaft and a head wider than said shaft, wherein said loops of said first and second suspension wires attach around said shafts of said front-facing post and said rear-facing post and are at least partially secured by said heads of said front-facing post and said rear-facing post.

7. A multi-configurable headset support system according to claim 6, wherein at least one of said front-facing post and said rear-facing post is retractably spring-biased into said earcup by a spring.

8. A multi-configurable headset support system according to claim 7, wherein force generated by said spring of said at least one of said front-facing post and said rear-facing post secures said loop disposed on said shaft against said earcup via said head.

9. A multi-configurable headset support system according to claim 6, said shaft comprising:

an outer tube fixedly secured to said earcup;

an inner plunger reciprocatably disposed inside said outer tube, said head attached to a distal end of said inner plunger; and a spring connecting said outer tube and said inner plunger biasing said inner plunger into said outer tube.

10. A multi-configurable headset support system according to claim 9, said outer tube comprising distal prongs and said head comprising key slots formed on a proximal surface of said head and configured to receive said distal prongs.

11. A multi-configurable headset support system according to claim 10, wherein said inner plunger is rotatable with respect to said outer tube when said inner plunger is at least partially withdrawn from said outer tube and said distal prongs are not in engagement with said key slots.

12. A multi-configurable headset support system according to claim 11, wherein when said inner plunger is at least partially withdrawn from said outer tube, said inner plunger is rotatable to a fixed extended position in which said distal prongs of said outer tube contact said proximal surface of said head and are not disposed in said key slots.

13. A multi-configurable headset support system according to claim 9, said shaft further comprising:

prongs formed on one of said outer tube and said head; and key slots formed on the other of said outer tube and said head and configured to receive said prongs.

14. A multi-configurable headset support system according to claim 13, wherein said inner plunger is rotatable with respect to said outer tube when said inner plunger is at least partially withdrawn from said outer tube and said prongs are not in engagement with said key slots.

15. A multi-configurable headset support system according to claim 14, wherein when said inner plunger is at least partially withdrawn from said outer tube, said inner plunger is rotatable to a fixed extended position in which said prongs are not disposed in said key slots.

16. A multi-configurable headset support system according to claim 6, said head comprising a proximal hub wider than said shaft, and said loops of said first and second suspension wires each comprising an opening wider than said shaft and narrower than said hub, wherein said hub fits within said loop secured on said shaft to help secure said loop on said earcup.

17. A multi-configurable headset support system according to claim 7, said head comprising a proximal hub wider than said shaft, and said loops of said first and second suspension wires each comprising an opening wider than said shaft and narrower than hub, wherein said hub fits within and is spring-biased within said loop secured on said shaft to help secure said loop on said earcup.

18. A multi-configurable headset support system according to claim 1, said earcup further comprising:

a speaker to provide sound to the wearer; and insulation configured to at least partially block external sounds from the wearer.

19. A multi-configurable headset support system according to claim 4, said earcups each further comprising:

a speaker to provide sound to the wearer; and insulation configured to at least partially block external sounds from the wearer.

20. A multi-configurable headset support system according to claim 5, said earcups each further comprising:

a speaker to provide sound to the wearer; and insulation configured to at least partially block external sounds from the wearer.

21. A multi-configurable headset support system enabling configuring of headset earcups in multiple ways on a user's head, comprising:
- at least one retractable post mounted on the earcup, said post having a longitudinal shaft and a head wider than said shaft;
- a suspension wire having a loop at an end of said wire, said loop configured to be releasably attachable to said retractable post when said post is in an extended position; and
- a support band securable to said suspension wire,
- wherein when said loop is attached to said shaft and said post is retracted to a retracted position, said head secures said loop against the earcup.

22. A multi-configurable headset support system according to claim 21, said shaft comprising:
- an outer tube fixedly secured to the earcup;
- an inner plunger reciprocatably disposed inside said outer tube, said head attached to a distal end of said inner plunger; and
- a spring connecting said outer tube and said inner plunger biasing said inner plunger into said outer tube.

23. A multi-configurable headset support system according to claim 22, said shaft further comprising:
- prongs formed on one of said outer tube and said head; and
- key slots formed on the other of said outer tube and said head and configured to receive said prongs.

24. A multi-configurable headset support system according to claim 23, wherein said inner plunger is rotatable with respect to said outer tube when said inner plunger is at least partially withdrawn from said outer tube and said prongs are not in engagement with said key slots.

25. A multi-configurable headset support system according to claim 22, said head comprising a proximal hub wider than said shaft, and said loop of said suspension wire comprising an opening wider than said shaft and narrower than hub,
- wherein said hub fits within and is spring-biased within said loop secured on said shaft to help secure said loop on the earcup.

* * * * *